United States Patent [19]

Inoue

[11] 4,453,545
[45] Jun. 12, 1984

[54] ENDOTRACHEAL TUBE WITH MOVABLE ENDOBRONCHIAL BLOCKER FOR ONE-LUNG ANESTHESIA

[76] Inventor: Hiroshi Inoue, No. 15-20, Shiratori 1-chome, Tama-ku, Kawasaki-shi, Kanagawa-ken, Japan

[21] Appl. No.: 373,311

[22] Filed: Apr. 29, 1982

[30] Foreign Application Priority Data

May 7, 1981 [JP] Japan .................................. 56-68698

[51] Int. Cl.³ .......................................... A61M 25/00
[52] U.S. Cl. ............................... 128/207.15; 128/911; 604/101
[58] Field of Search ...................... 128/204.28, 207.14, 128/207.15, 260.26; 604/96, 95, 97–103, 158, 280

[56] References Cited

U.S. PATENT DOCUMENTS

| | | | |
|---|---|---|---|
| 3,322,126 | 5/1967 | Rusch et al. .................... | 128/207.15 |
| 4,090,518 | 5/1978 | Elam ............................... | 128/207.15 |
| 4,231,365 | 11/1980 | Scarberry ....................... | 128/207.15 |
| 4,233,984 | 11/1980 | Walling .......................... | 128/207.14 |
| 4,248,221 | 2/1981 | Winnard ......................... | 128/207.15 |
| 4,327,720 | 5/1982 | Bronson et al. ................ | 128/207.15 |

FOREIGN PATENT DOCUMENTS 708477  5/1954  United Kingdom ................ 604/101

OTHER PUBLICATIONS

Inoue et al., "New Device for One-Lung Anesthesia: Endotracheal Tube with Movable Blocker" Article.
Kaplan, "Thoracic Anesthesia" Article.
Ginsberg, "New Technique for One-Lung Anesthesia Using an Endobronchial Blocker" Article.

Primary Examiner—Henry J. Recla
Assistant Examiner—Karin M. Reichle
Attorney, Agent, or Firm—Flynn, Thiel, Boutell & Tanis

[57] ABSTRACT

An endotracheal tube with movable endobronchial blocker for one-lung anesthesia is disclosed comprising an endotracheal tube with a a cuff having a small channel formed within the wall of the endotracheal tube along almost the entire length thereof and a catheter with a cuff for endobronchial blockade called an endobronchial blocker which is housed in the small channel and can be let out when in use.

13 Claims, 13 Drawing Figures

ENDOTRACHEAL TUBE WITH MOVABLE ENDOBRONCHIAL BLOCKER FOR ONE-LUNG ANESTHESIA

BACKGROUND OF THE INVENTION

1. Field of the Invention:

The present invention relates to an endotracheal tube with a movable endobronchial blocker for one-lung anesthesia which is capable of accomplishing collapse of the operated lung with the usual technique for endotracheal intubation.

2. Description of the Prior Art:

Operations for lung cancer, esophageal cancer, thoracic aorta, etc. that need a thoracotomy are often disturbed by lung ventilation. Keeping such a lung depressed with a retractor may damage the lung. On the other hand, it has been confirmed by many researches, in the case of a patient who is certain to stand the aforesaid operations judging from his cardiopulmonary function, there is not any anesthetic trouble and danger during operation, even if the contralateral lung alone is ventilated, in other words even if the operated lung is completely collapsed. This technique is named "one-lung anesthesia". One-lung anesthesia can be of great assistance to the surgeon not only during operations on the lungs but also to provide better exposure for operations on the oesophagus, mediastinum and thoracic aorta.

Hitherto, one-lung anesthesia has been accomplished by the use of either single-lumen endobronchial tube which is placed in the main bronchus or double-lumen endobronchial tube invented by Carlens and Robertshaw. These tubes, however, have serious drawbacks and have not been used widely.

Figure 1A:
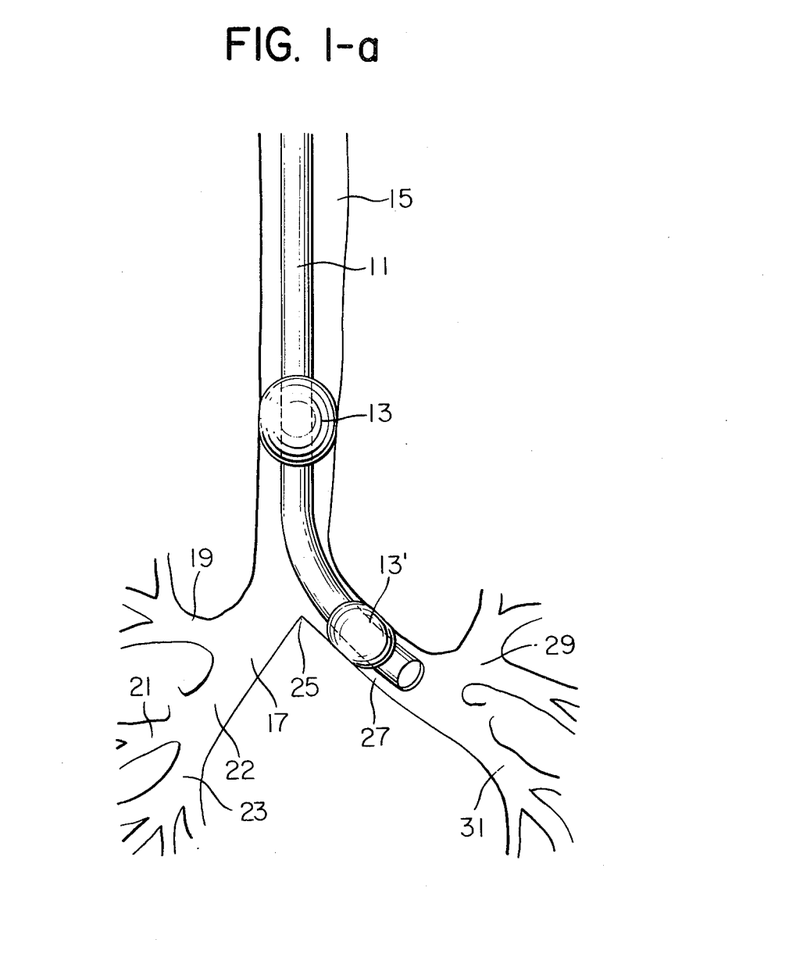
Figure 1B:
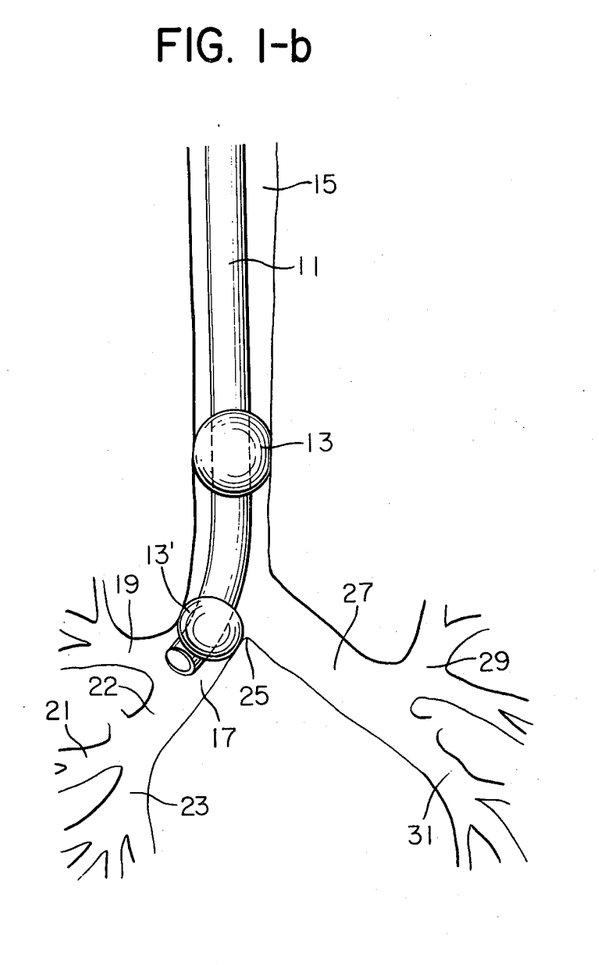

The conventional single-lumen endobronchial tube 11 is described with reference to FIG. 1-a and FIG. 1-b. The single-lumen endobronchial tube 11 is essentially a tube having cuffs 13 and 13'. It comes in two types: one for the left one-lung anesthesia (FIG. 1-a) and the other for the right one-lung anesthesia (FIG. 1-b). It is simple in structure, but has the following disadvantages.

(a) In order to accomplish the right one-lung anesthesia, it is necessary to position the end of the tube at the right main bronchus 17 as shown in FIG. 1-b. The branch-off point of the right upper lobe 19 is very close to the bifurcation of the trachea 15. In other words, the right main bronchus 17 is short (usually 1.5 cm or less) by nature. Therefore, there often arises an occasion that the end of the tube goes beyond the branch-off point of the right upper lobe 19, with the result that ventilation takes place only in the right middle and lower lobes of the right lung. In FIG. 1-b, the right middle bronchus, the right lower bronchus, and the intermediate bronchus are indicated by the reference numerals 21, 23 and 22, respectively. The left main bronchus, the left upper lobe bronchus, and the left lower lobe bronchus are indicated by the reference numerals 27, 29 and 31, respectively.

(b) Each time when it becomes necessary to inflate the collapsed lung during anesthesia, the tube 11 placed in the bronchus should be retracted to the trachea 15. And, after inflation of the operated lung, the tube should be inserted again into the main bronchus of the non-operated lung.

Figure 2:
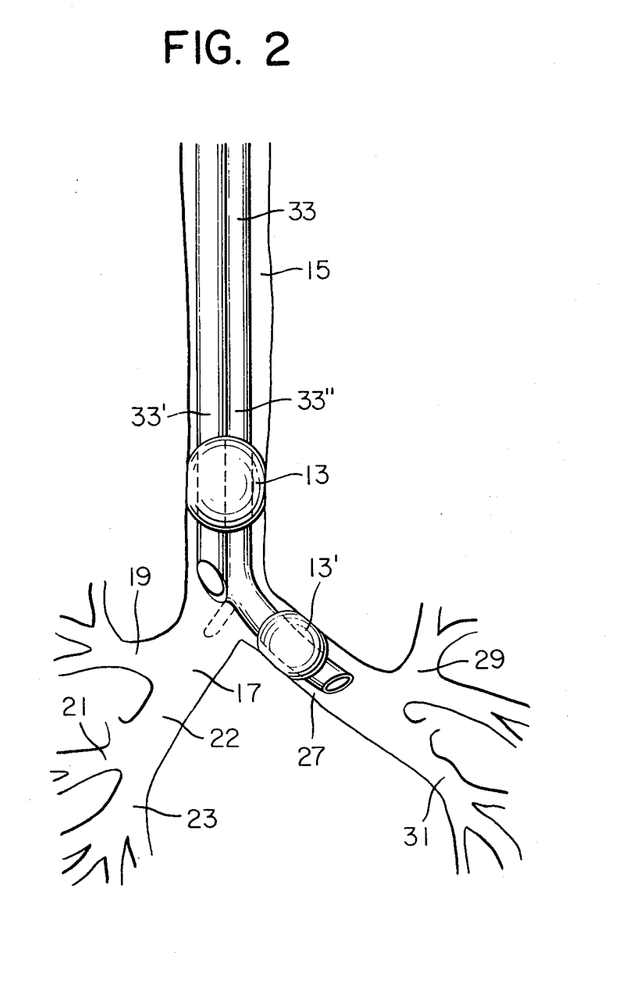
FIG. 2 illustrates a conventional double-lumen endobronchial tube.

On the other hand, the double-lumen endobroncial tube is essentially a tube 33 integrally made up of a tube 33' for ventilating the right lung and a tube 33" for ventilating the left lung, the tube 33" being longer than the tube 33', as shown in FIG. 2. It was originally a rubber tube devised by Carlens for bronchospirometry, and it has the following disadvantages when used for one-lung anesthesia.

(a) Insertion requires a certain degree of skill.

(b) It is difficult to keep the tube fixed at a predetermined position, after insertion, and the tube often enters deep over the position or comes out during anesthesia. In other words, the tube is not stable.

In addition, the aforementioned two types of tubes have disadvantages by nature, the opening of the tubes being inevitably small in the inside diameter and the length of the tubes being long as compared with the endotracheal tube.

SUMMARY OF THE INVENTION

It is an object of the present invention to provide an endotracheal tube with a movable endobronchial blocker for one-lung anesthesia which is free from the aforesaid disadvantages and which can provide collapse of operated lung with ease and safety.

It is another object of the present invention to provide an endotracheal tube with a movable endobronchial blocker which is highly stable when inserted into the bronchus.

According to the present invention, the endotracheal tube with movable endobronchial blocker for one-lung anesthesia comprises an endotracheal tube with a cuff having a small channel formed within the wall of the endotracheal tube along almost the entire length thereof and a catheter with a cuff for endobronchial blockade called an endobronchial blocker, which is housed in the small channel and can be let out when in use.

When in use, the endotracheal tube of this invention which houses the endobronchial blocker is inserted into the trachea and the cuff of the endotracheal tube is inflated with air, and then the endobronchial blocker is let out and inserted into the bronchus and the cuff of the blocker is inflated with air, whereby one-lung anesthesia can be accomplished. If necessary, immediate shifting to bilateral ventilation is possible by deflation of the cuff of the blocker.

BRIEF DESCRIPTION OF THE DRAWINGS

FIG. 1-a and FIG. 1-b illustrate a conventional single-lumen endobronchial tube.

FIG. 3-a is a perspective view of the endotracheal tube of this invention.

FIG. 3-b is a sectional view taken along line A—A in FIG. 3-a.

FIG. 4-a is a perspective view of the endobronchial blocker of this invention.

FIG. 4-b and FIG. 4-c are sectional views taken along lines B—B and C—C, respectively, in FIG. 4-a.

FIG. 7-a and FIG. 7-b illustrate one-lung anesthesia for the right lung being performed by using the endotracheal tube with movable endobronchial blocker for one-lung anesthesia of this invention.

DETAILED DESCRIPTION OF THE PREFERRED EMBODIMENTS

Figures 3A, 3B:
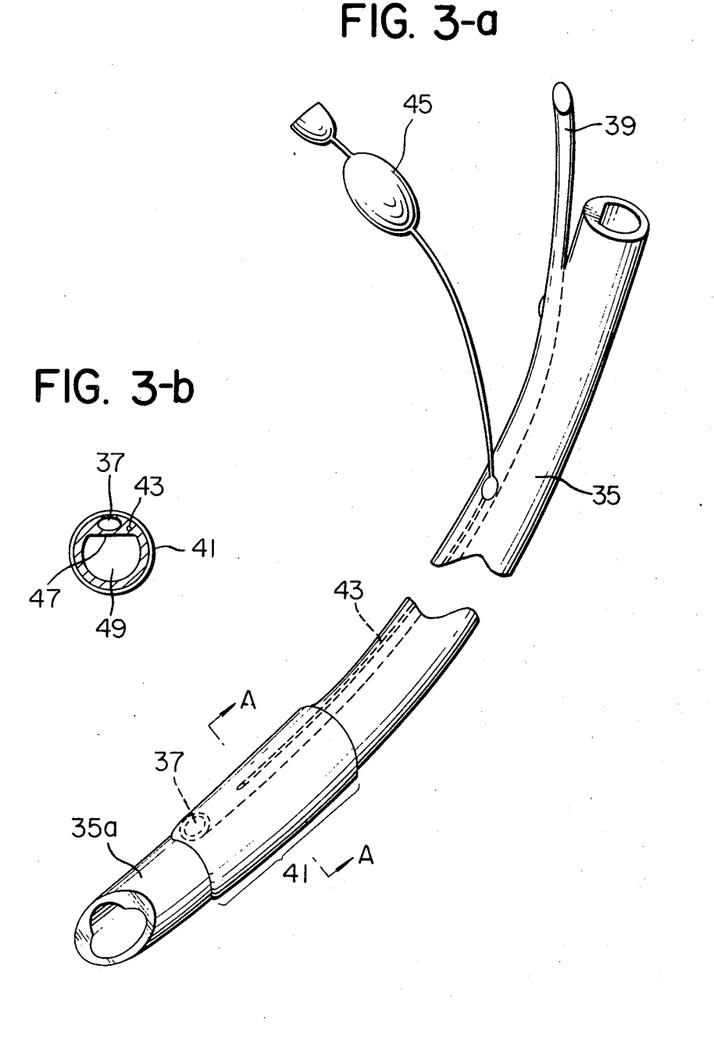

FIG. 3-a is a perspective view of an example of the endotracheal tube of this invention, and FIG. 3-b is a sectional view along line A—A in FIG. 3-a. This tube may be made of silicone and the like.

The endotracheal tube 35 is similar to a conventional endotracheal tube in external appearance except that it has a branching guide tube 39 which communicates with the channel 37 and projects about 3 cm in the direction toward the upper opening of the tube 35. The guide tube 39 has, for example, an inside diameter of about 3.5 mm or an oval section of 3 mm by 4 mm. The tube 35 has a cuff 41 near the end 35a thereof, and the cuff 41 communicates with an air blowing means 45 through an air supply duct 43 for cuff inflation. The small channel 37 extending along almost the entire length of the tube is formed in the concavely curved wall of the tube by simultaneous molding or bonding. Therefore, the ventilation duct 49 is adjacent to the small channel 37 but is separated therefrom by the partition wall 47 in the section as shown in FIG. 3-b.

At the part several centimeters away from the end of the endotracheal tube 35, the partition wall 47 separating the small channel 37 from the ventilation duct 49 may be omitted as shown in FIG. 3-a. In such a structure, the small channel 37 may have the same tunnel-like shape as the branching guide tube 39. In this tunnel-like channel and branching guide tube is housed the catheter part of the endobronchial blocker, and in the forward end of the endotracheal tube where there is no partition wall is housed the cuff of the catheter. Consequently, the part near the forward end of the endobronchial blocker can be shaped with great freedom. Needless to say, it is also possible to provide the small channel 37 up to the forward end of endotracheal tube by forming the partition wall 47 as far as the forward end of the endotracheal tube. The branching guide tube 39 is intended to facilitate the manipulation of the endobronchial blocker.

Figures 4A, 4B, 4C:
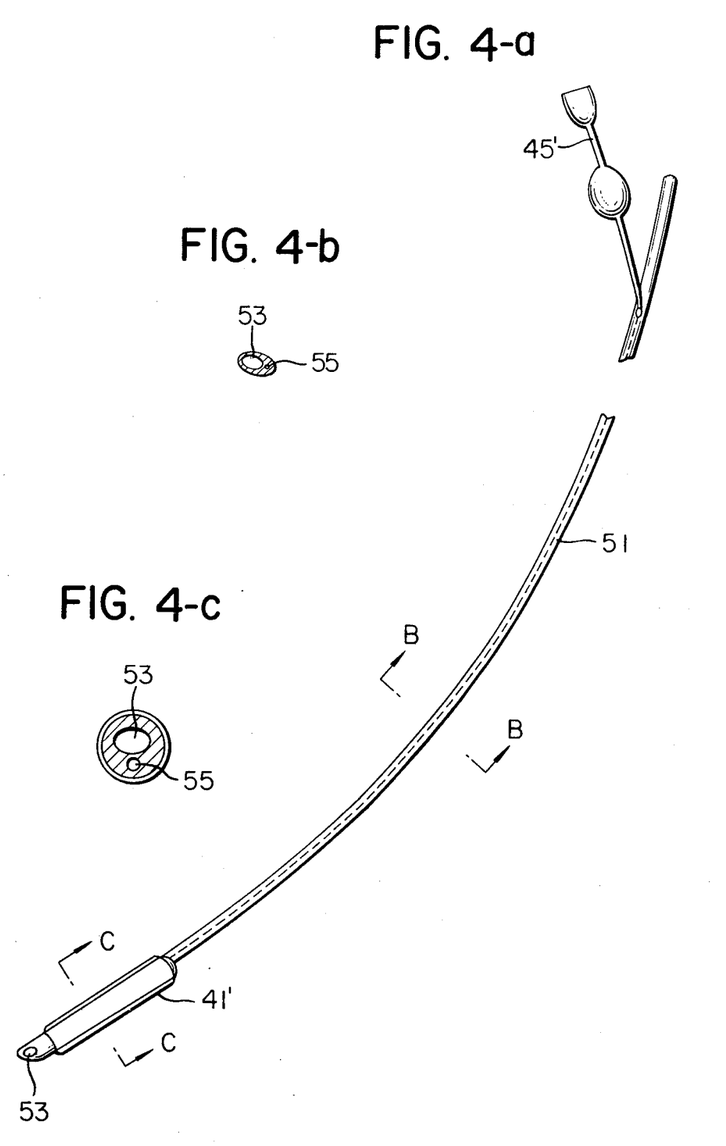
Figure 5:
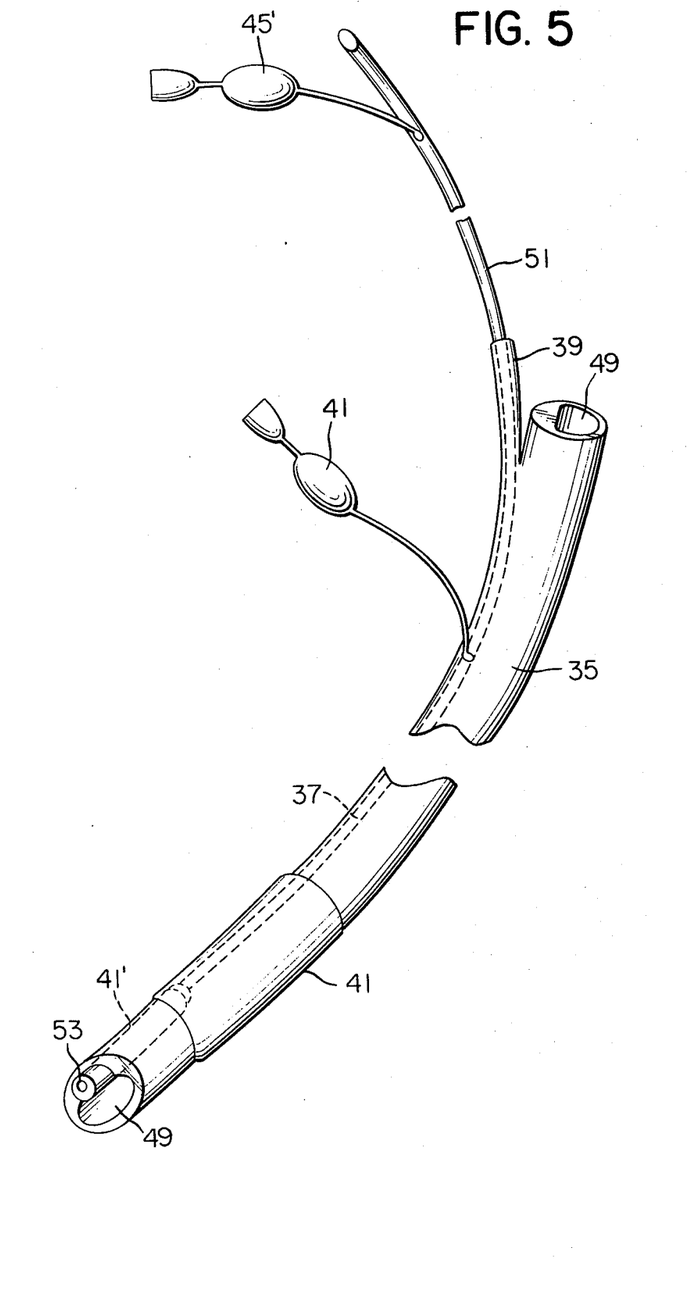
FIG. 5 is a perspective view of the endotracheal tube with movable endobronchial blocker for one-lung anesthesia of this invention.

FIG. 4-a shows the endobronchial blocker 51 which is inserted and housed in the small channel 37 of the endotracheal tube 35 as shown in FIG. 3. As illustrated in FIG. 4-b, the catheter part of the endobronchial blocker (about 40 cm long) has the duct 53 for aspiration of gas or bronchial secretion from the blocked bronchus. Note the small duct 55 for inflation of the cuff 41 of the endobronchial blocker by the cuff inflating means 45'. The duct 53 may be omitted depending on the usage. As shown in the sectional view of FIG. 4-c, the forward end of the catheter of the endobronchial blocker to which the low-pressure high-volume cuff 41' about 3.5 cm long is attached may be larger in diameter (about 5 mm) and have a circular cross section. By forcing air into this part, the main bronchus can be blocked with the cuff. Needless to say, it is possible to make the diameter of the catheter of the endobronchial blocker substantially the same throughout the entire length. It is desirable that the endobronchial blocker 51 is slightly curved over the entire length. As shown in FIG. 5, the endobronchial blocker 51 is housed initially in the small channel 37 of the endotracheal tube 35 in such a manner that it can be moved smoothly in the channel 37. When not in use, they may be stored separately.

Figure 6:
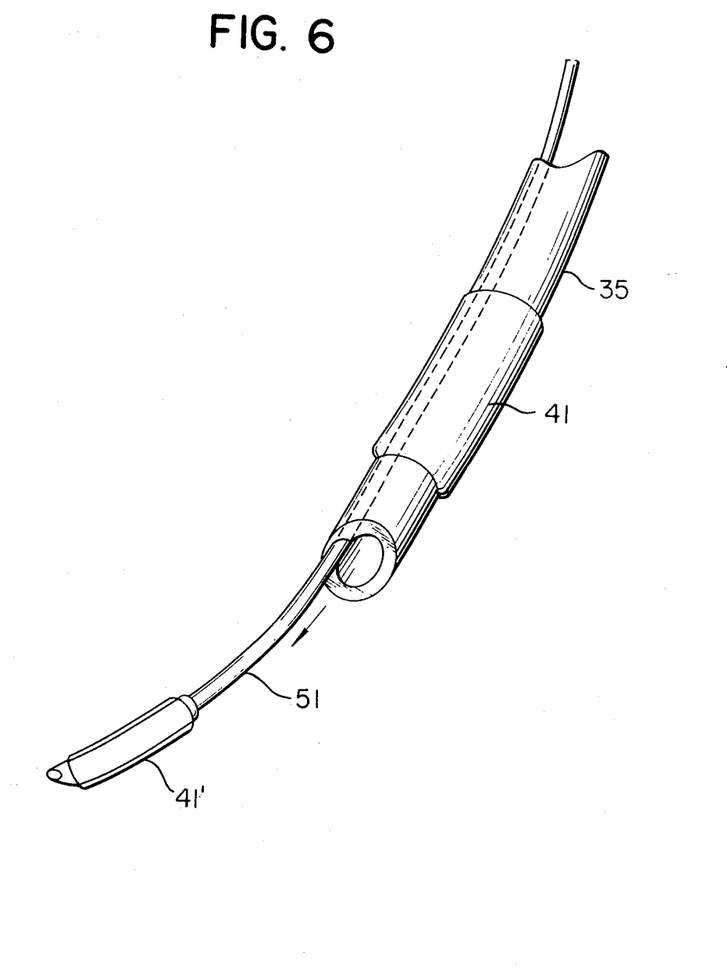
FIG. 6 is a perspective view showing the endobronchial blocker which is being let out from the small channel in the endotracheal tube.

FIG. 6 shows the relative position of the endotracheal tube 35 of this invention and the endobronchial blocker 51 in use. The endobronchial blocker 51 is let out from the forward end of the endotracheal tube 35 so that the endobronchial blocker is inserted into the targeted main bronchus. The bronchus of the operated lung is then ready to be blocked.

Figure 7A:
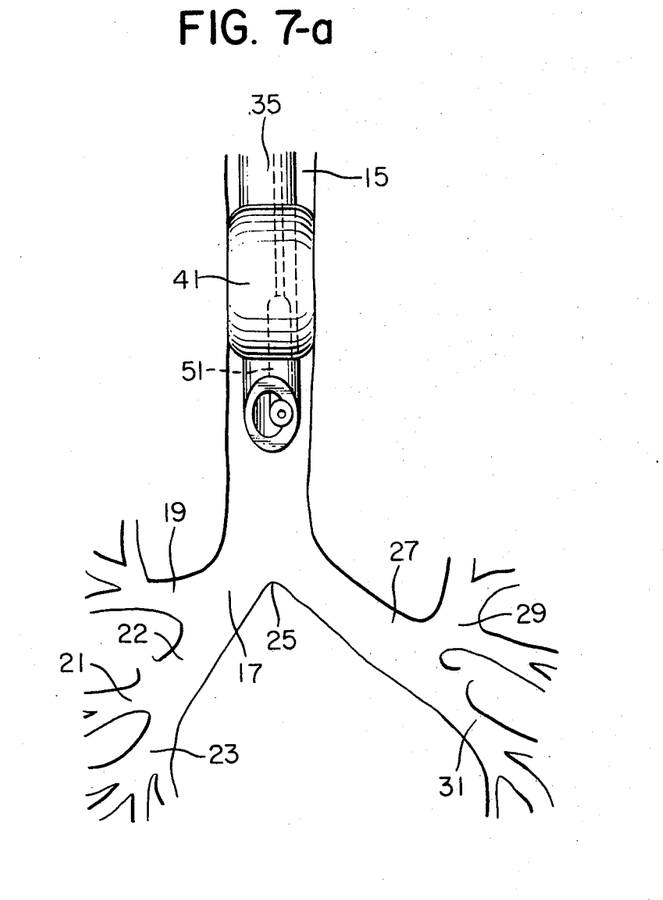
Figure 7B:
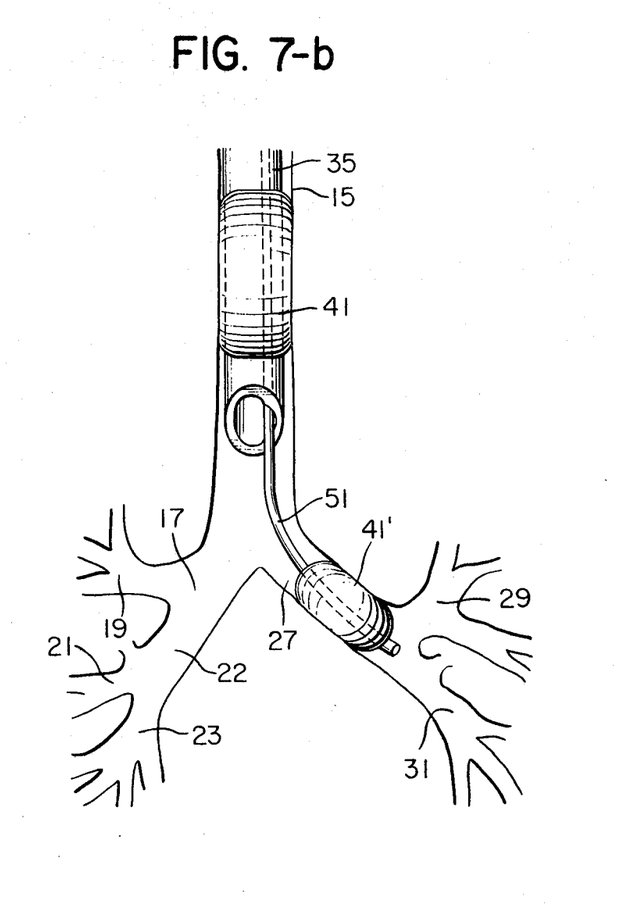

The endotracheal tube of this invention can be used in the following manner. As shown in FIG. 7-a and FIG. 7-b, at first, the endotracheal tube with movable endobronchial blocker for one-lung anesthesia is inserted into the trachea 15 of a patient by a usual method. If right one-lung anesthesia is to be performed during operations, the inserted endotracheal tube 35 is turned (axially) counterclockwise so that the channel (or the endobronchial blocker 51) is directed to the left and the cuff 41 of the endotracheal tube 35 is inflated to fix the tube in position (FIG. 7-a). Then, the endobronchial blocker 51 is let out as far as the marked position (about 6 cm). Since the endobronchial blocker 51 is formed so that it is curved outward, the forward end of the endobronchial blocker is moved forward while being kept in contact with the left wall of the trachea. Thus, the forward end of the endobronchial blocker 51 is inserted easily and certainly into the left bronchus, and the left bronchus 27 is blocked with certainty by the cuff 41' (FIG. 7-b).

Figure 8:
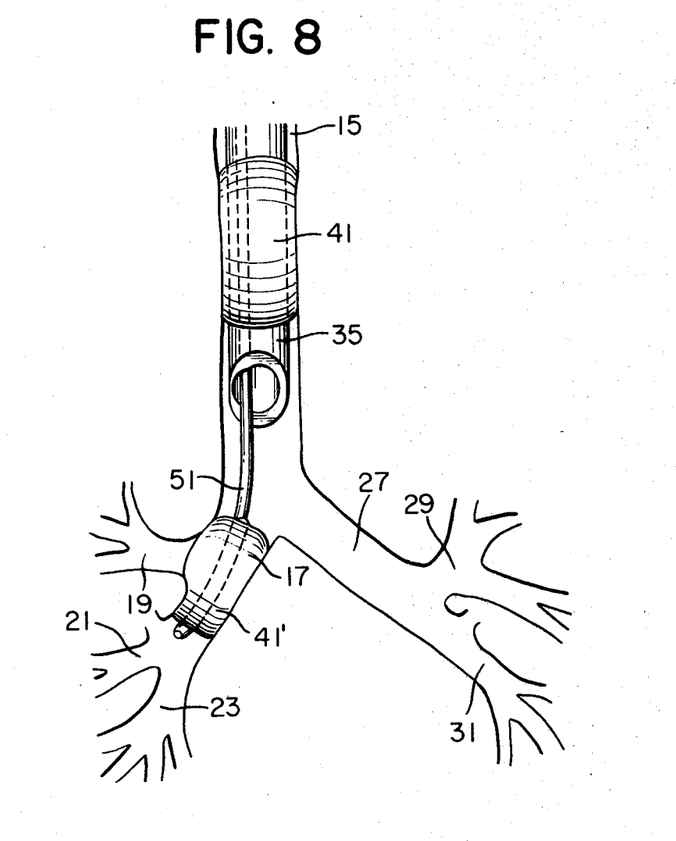
FIG. 8 illustrates one-lung anesthesia for the left lung being performed by using the endotracheal tube with movable endobronchial blocker for one-lung anesthesia of this invention.

On the other hand, if the left one-lung anesthesia is to be performed during operations, the inserted endotracheal tube 35 is turned (axially) clockwise so that the channel is directed to the right and the endobronchial blocker 51 is inserted into the right bronchus 17 as above and the cuff 41' is expanded, as shown in FIG. 8.

Whether or not the endobronchial blocker has been inserted correctly into bronchus of the targeted side may be confirmed by the aid of chest roentgenogram or flexible bronchofiberscope. Needless to say, a skilled chest surgeon will be able to determine the position of the cuff of the endobronchial blocker readily by palpatation of the bronchus.

The endotracheal tube of this invention has the structure and the effect as mentioned above and is free of the disadvantages of the conventional single-lumen endobronchial tubes and double-lumen endobronchial tubes.

In addition, since the tube of this invention is an endotracheal tube it can be made larger in inside diameter and shorter in length than the conventional endobronchial tube for one-lung anesthesia.

In case any trouble which is considered due to one-lung anesthesia should occur during anesthesia by unilateral ventilation, or one-lung anesthesia with the tube of this invention, it is possible to readily shift to bilateral ventilation simply by evacuation of the cuff which is blocking the bronchus.

Thus, the tube of this invention is simpler and safer to operate than the conventional endobronchial tube for one-lung anesthesia, and has a great effect.

It should be understood that the foregoing relates to only a preferred embodiment of the invention and the invention is not limited thereto.

What is claimed is:

1. An apparatus adapted to be used for carrying out one-lung anesthesia, comprising:
    an elongated endotracheal tube adapted to be inserted into a human trachea and having a forward end, a rear end and a length sufficient to allow the forward end of said tube to be positioned in the trachea at a location near the bifurcation of the trachea into right and left main bronchi; said tube having wall means and an inner surface, the inner surface of said tube defining an internal central lumen extending lengthwise within said tube, said wall means defining an elongated channel which extends in the lengthwise direction of said tube for almost the entire length of said tube, the axis of said channel being offset radially outwardly from the central axis of said tube and being smaller in cross sectional area than said lumen;

a first inflatable cuff mounted on the outer periphery of said tube near the forward end thereof, said first cuff being adapted upon inflation thereof to expand into substantial sealing contact with the inner surface of the trachea near the bifurcation thereof; and an endobronchial blocker comprising an elongated catheter which is received in said channel for longitudinal sliding movement therein, said catheter having a forward end and at least one duct extending lengthwise therein, and a second inflatable cuff mounted on the outer periphery of said catheter near the forward end thereof, said duct being in communication with said second cuff so that said second cuff can be inflated by gas supplied through said duct, said second cuff being longitudinally slidably receivable within the forward end of said endotracheal tube so that after said endotracheal tube has been inserted into the trachea near the bifurcation thereof, the forward end of said endobronchial blocker can be slidably extended from the forward end of said endotracheal tube into a main bronchus following which said second cuff can be inflated into substantial sealing contact with the inner surface of said main bronchus.

2. An apparatus as claimed in claim 1, in which said channel is formed within the wall of said endotracheal tube.

3. An apparatus as claimed in claim 2, in which said endotracheal tube has a tubular wall defining said lumen and a partition wall which extends along the length of said tube from a location near to but spaced from the forward end thereof toward the rearward end of said endotracheal tube, said partition wall isolating said channel from said lumen in a direction rearwardly from said location, said channel and said lumen being in direct communication with each other forwardly of said location.

4. An apparatus as claimed in claim 1 or claim 2, wherein said endotracheal tube is curved in the lengthwise direction thereof in the shape of a concavo-convex curve, and said channel is formed on the concavely curved side of said endotracheal tube.

5. An apparatus as claimed in claim 4, wherein said catheter is curved.

6. An apparatus as claimed in claim 5, in which said endotracheal tube has a tubular wall defining said lumen and a partition wall which extends along the length of said tube from a location near to but spaced from the forward end thereof toward the rearward end of said endotracheal tube, said partition wall isolating said channel from said lumen in a direction rearwardly from said location, said channel and said lumen being in direct communication with each other forwardly of said location.

7. An apparatus as claimed in claim 5, further comprising a branching guide tube which branches from said endotracheal tube and projects toward the rear end thereof, said branching guide tube being in communication with said channel, said endobronchial blocker slidably extending through said branching guide tube.

8. An apparatus as claimed in claim 5, wherein said catheter has a second duct therein adapted for aspirating material therethrough, said second duct opening near the forward end of said catheter and extending therefrom rearwardly along the length of said catheter.

9. An apparatus as claimed in claim 1 or claim 2, further comprising a branching guide tube which branches from said endotracheal tube and projects toward the rear end thereof, said branching guide tube being in communication with said channel, said endobronchial blocker slidably extending through said branching guide tube.

10. An apparatus as claimed in claim 1 or claim 2, wherein said catheter is curved.

11. An apparatus as claimed in claim 1 or claim 2, wherein said catheter has a second duct therein adapted for aspirating material therethrough, said second duct opening near the forward end of said catheter and extending therefrom rearwardly along the length of said catheter.

12. An apparatus as claimed in claim 1 or claim 2, wherein the forward end portion of said catheter having said second cuff mounted thereon is of larger diameter than the remainder of said catheter extending rearwardly therefrom.

13. An apparatus as claimed in claim 1 or claim 2, further comprising a first cuff inflating device adapted for reversibly inflating said first inflatable cuff, and a second cuff inflating device in communication with said duct adapted for reversibly inflating said second inflatable cuff.

* * * * *